United States Patent
Shaw

(10) Patent No.: US 6,357,445 B1
(45) Date of Patent: Mar. 19, 2002

(54) SURGICAL DRAPE FOR COLONOSCOPY

(76) Inventor: Timothy A. Shaw, 450 W. 11th St., Eagar, AZ (US) 85925

( * ) Notice: Subject to any disclaimer, the term of this patent is extended or adjusted under 35 U.S.C. 154(b) by 0 days.

(21) Appl. No.: 09/659,385

(22) Filed: Sep. 11, 2000

(51) Int. Cl.⁷ .............................................. A61B 19/00
(52) U.S. Cl. ..................................... 128/849; 128/853
(58) Field of Search ................................ 128/849–856

(56) References Cited

U.S. PATENT DOCUMENTS

| | | | |
|---|---|---|---|
| 2,662,525 A | 12/1953 | Priebe | 128/283 |
| 2,688,327 A | 9/1954 | Berg | 128/283 |
| 2,778,362 A | 1/1957 | Pollock et al. | 128/283 |
| 2,788,785 A | 4/1957 | Present | 128/283 |
| 4,414,968 A * | 11/1983 | Amin | 128/853 |
| 4,462,396 A | 7/1984 | Wichman | 128/132 D |
| 4,476,860 A * | 10/1984 | Collins | 128/853 |
| 4,570,628 A * | 2/1986 | Neal | 128/853 |
| 4,598,458 A * | 7/1986 | McAllester | 128/853 |
| 4,681,574 A | 7/1987 | Eastman | 604/344 |
| 5,026,362 A | 6/1991 | Willett | 604/345 |
| 5,125,916 A | 6/1992 | Panebianco et al. | 604/332 |
| 5,388,593 A * | 2/1995 | Thomalla | 128/849 |

OTHER PUBLICATIONS

Pending Patent, Serial No. 08/964,511, Filing date Nov. 5, 1997, "Surgical Drape for Colonoscopy", Timothy A. Shaw.

* cited by examiner

Primary Examiner—Michael A. Brown
(74) Attorney, Agent, or Firm—Schmeiser, Olsen & Watta

(57) ABSTRACT

A flexible surgical drape has an adhesive side and a non-adhesive side. The adhesive side is adhesive across substantially its entire face. The drape consists of a flexible sheet suitable for covering a substantial portion of a patient's body. A pocket for catching patient secretions and other fluids is attached to the adhesive side of the drape. The drape contains an opening capable of receiving a removable valve, which, when in place, seals off the opening and prevents the passage of gases, secretions, and fluids that are typically present during a medical procedure. The valve can be made to lock into the opening so as to reduce the likelihood of its inadvertent removal. An examining tool such as a colonoscope fits through a hole extending through the valve and thus can be passed from one side of the drape to the other. A reservoir suitable for holding a lubricating substance is securely attached to and forms part of the valve, and the examining tool when inserted through the valve passes through this lubricating substance and is coated by it.

21 Claims, 5 Drawing Sheets

SURGICAL DRAPE FOR COLONOSCOPY

BACKGROUND OF THE INVENTION

1. Technical Field

This invention generally relates to a protective barrier for use in a medical setting, and more specifically relates to a surgical drape designed to protect medical personnel from bodily fluids, excretions, and other contaminants likely to be present during a medical procedure. The invention is particularly suited for use during a colonoscopy but would be useful in conjunction with any procedure in which contamination from patient secretions is a concern and where a tubular examining tool is used.

2. Background Art

A colonoscopy is a procedure in which the inside of the colon is examined using a long, flexible, fiber-optic viewing instrument called a colonoscope. The colon is located in the abdominal cavity and forms part of the large intestine. It is subject to various disorders, the diagnosis and treatment of which can sometimes be aided by the close-up view that a colonoscope provides. Besides providing a clearer visual picture of the colon, a colonoscope can also be fitted with a variety of attachments used by the examining physician to, for example, take biopsy specimens or remove unwanted growths from the colon's interior.

A physician performs a colonoscopy by lubricating the colonoscope and inserting it through the anus into the colon, which is inflated with air. As the scope is guided by the physician along the length of the colon it generates images that appear on a viewing device. The need to move the colonoscope to various locations within the colon during the procedure requires that the examining physician be in close proximity with the patient at all times during the exam.

In almost every colonoscopy, the air used to inflate the colon forces some of the colon's contents out of the anus. This includes undigested material not eliminated beforehand, the lubricant used to coat the colonoscope, and other colonic secretions. The laxatives typically taken by a patient prior to the exam tend to increase this effect. These expelled secretions obviously present a risk of contamination, a risk that becomes even greater if, as is often the case, the secretions are aerosolized, thereby contaminating the air of the examining room. Because of the requirement of close doctor-patient proximity during a colonoscopy, such expelled and aerosolized excretions present a serious health risk to medical personnel.

Basic precautions against contamination such as gloves and face masks offer some protection but are imperfect in that they permit the passage of contaminated substances around their edges or through tears or other openings in them. Surgical drapes generally provide a sanitary work area but do not provide protection from bodily fluids and excretions.

U.S. Pat. No. 5,960,794 granted Oct. 5, 1999 to the present inventor for "SURGICAL DRAPE" describes a drape with an adhesive periphery consisting of a flexible sheet having a valve thereon for maintaining a barrier between the patient and doctor during a medical procedure and allowing for the passage of a surgical instrument therethrough. During a colonoscopy an examining tool is inserted into the colon through the anus, a delicate and potentially painful process. The ability to see clearly what one is doing becomes very important for the medical worker performing this procedure. Therefore, providing a surgical drape that will allow good visibility would increase the ease with which the tool is inserted.

With prior U.S. Pat. No. 5,960,794 the drape is adhesive only in a small region around its periphery. This can lead to the need to stop the examination in order to reposition the drape if the seal between the patient and the drape is lost.

DISCLOSURE OF INVENTION

Therefore, there existed a need to provide a surgical drape suitable to protect a doctor and attending personnel from contamination during a medical procedure. The present invention is particularly suited to procedures such as a colonoscopy where patient excretions are typically present and there is a high risk of contaminant aerosolization.

According to the present invention, a flexible surgical drape has an adhesive side and a non-adhesive side. The adhesive side is adhesive across substantially its entire face. The drape consists of a flexible sheet suitable for covering a substantial portion of a patient's body. A pocket for catching patient secretions and other fluids is attached to the adhesive side of the drape. The pocket is also adhesive so that it can be securely affixed to the patient's body in the location where it will best catch such secretions. The drape contains an opening capable of receiving a removable insert which, when in place, seals off the opening and prevents the passage of gases, secretions, and fluids that are typically present during a colonoscopy. The insert is made to lock into the opening so as to reduce the likelihood of its inadvertent removal. The insert may also be thought of as a valve, in that an examining tool, such as a colonoscope, fits through a hole extending through the valve and thus can be passed from one side of the drape to the other. The insert will be referred to hereinafter as a valve.

The valve in its preferred embodiment has the general shape of a disk containing a small, hollow column in its center through which the colonoscope is passed, although other configurations are also possible. For example, any structure such as flaps that would create a collar around the colonoscope yet allow the colonoscope to be inserted and withdrawn through the opening would be acceptable. A reservoir suitable for holding a lubricating substance is securely attached to and forms part of the valve, and the colonoscope when inserted through the valve passes through this lubricating substance and is coated by it. The periphery of the valve structure contains the locking and sealing mechanism.

The continuously adhesive face of the drape facilitates its attachment to the patient in a way such that it contains patient secretions and keeps them away from the medical personnel performing the procedure. The fact that the valve is removable increases doctor visibility and the maneuverability of the scope, both of which aid in the scope insertion process. In rare cases, perhaps one out of a thousand, the physician will collect from the colon a specimen, possibly a polyp or part of a tumor, that is so large it must be removed before the examination can proceed. A removable valve in those instances provides the further advantage of allowing specimen removal after merely unlocking and displacing the valve. The entire drape need not be withdrawn and repositioned but can be left undisturbed.

The foregoing and other features and advantages of the invention will be apparent from the following more particular description of preferred embodiments of the invention, as illustrated in the accompanying drawings.

BRIEF DESCRIPTION OF DRAWINGS

The preferred embodiments of the present invention will hereinafter be described in conjunction with the appended drawings, where like designations denote like elements.

MODES FOR CARRYING OUT THE INVENTION

Figure 1:
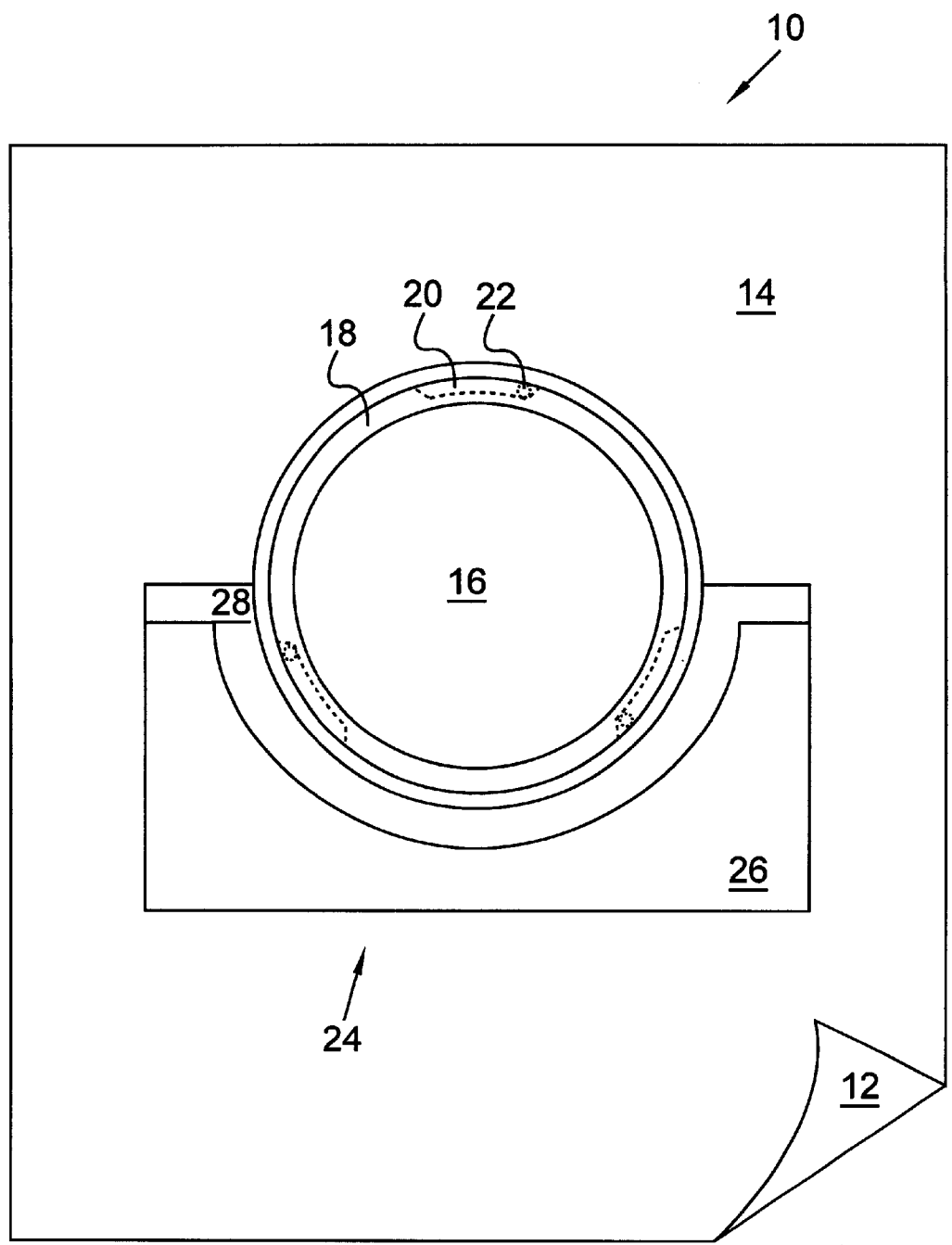
FIG. 1 is a top view of the underside of the surgical drape of the present invention with the valve removed.

Referring now to FIG. 1, surgical drape 10 has non-adhesive side 12 and adhesive side 14. Drape 10 forms a substantially fluid-impermeable barrier between medical personnel and patient during a medical procedure. Adhesive side 14 is adhesive across substantially its entire face. Drape 10 is provided with opening 16 and ledge 18, opening 16 capable of receiving a removable valve and having flanges 20 which form part of the mechanism that locks the removable valve in place. Each flange 20 includes a flange finger 22. Flanges 20 and flange fingers 22 are drawn with dashed lines to indicate that in this view they are behind ledge 18 and would not be visible when looking at adhesive side 14 of drape 10. The locking mechanism will be further illustrated in connection with FIG. 4. Opening 16 is preferably located near the center of drape 10, but can be placed at other locations.

Ledge 18 provides a seat for a gasket attached to the removable valve. When the valve is inserted in opening 16, the gasket, shown in FIG. 3, settles onto ledge 18, thereby forming a seal between the valve and rim 18. Note that the valve is inserted from non-adhesive side 12 of drape 10 and thus the gasket sits on the side of ledge 18 not shown in this figure. Pocket 24 is disposed on adhesive side 14 of drape 10 in a location suitable for catching and containing secretions and other discharge from a patient and has lower surface 26 and upper surface 28. Lower surface 26 is adhesive and upper surface 28 is non-adhesive.

Adhesive side 14 eases the secure attachment of drape 10 to a patient. It is originally protected with an easily removable, non-adhesive peel-off cover, not shown, designed to prevent adhesion of drape 10 before such adhesion is desired. In one embodiment of the present invention, the peel-off cover is made of absorbent material and is adapted to be placed on the examination table under the patient. Being adhesive across substantially its entire surface, rather than simply around its periphery, adhesive side 14 can adhere to every inch of a patient's body that it touches, thus greatly lessening the chance that it will slip or lose its seal during the examination. For example, drape 10 can be positioned between the legs of a patient, who lie on his or her side during a colonoscopy, and can then be pressed onto the skin of both the inner and outer thigh as well as the person's hips, back, and sides. With that degree of coverage, the continuous adhesive is well suited to forming a secure seal that holds until no longer needed.

With a colonoscope inserted into a patient's colon, the patient has no control over the discharge of secretions from the colon through the anus. Although the colon typically will have been largely cleansed, using a variety of methods, prior to the colonoscopy, some colonic substances remain and these, along with the air and lubricating solution introduced to facilitate the examination process, exit the anus during the procedure. Pocket 24 is placed so as to catch and contain this discharge. Lower surface 26 adheres to the patient's body while upper surface 28 remains unattached. The back flow of air as it leaves the colon acts to hold the surfaces apart and provide a cavity between them suitable for the collection of the discharge. When the colonoscopy is finished, drape 10 is removed from the patient and carefully rolled up, with pocket 24 interior to the roll, and deposited in a contaminated waste container for disposal.

Figure 2:
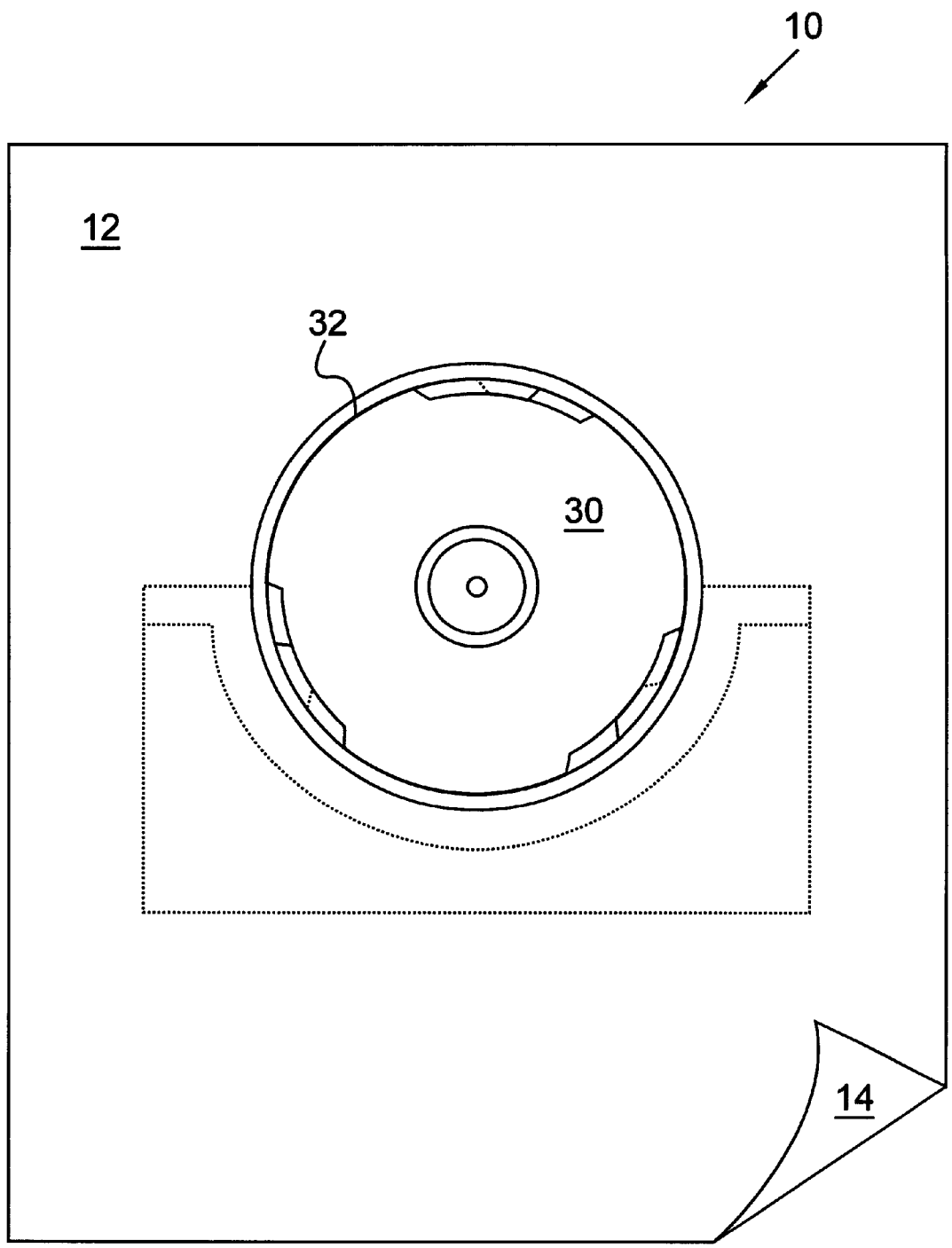
FIG. 2 is a top view of the surgical drape with the removable valve inserted.

Referring now to FIG. 2, removable valve 30 is disposed in opening 16 (shown in FIG. 1) of drape 10. Note that this view is of non-adhesive side 12 of the drape. This is the side from which valve 30 is inserted into opening 16. Valve 30 has periphery 32. Pocket 24 is drawn with dashed lines to indicate its location on the underside of drape 10 as seen from this side. In its preferred embodiment removable valve 30 has a circular shape but other designs are also possible. For example it should be understood that a valve having a variety of other simple shapes, such as a square, rectangle, or triangle, would serve the purposes of the present invention.

Valve 30 is typically about four inches in diameter, although smaller or larger sizes are equally possible. It fits snugly into opening 16 and forms a seal, using gasket 46 shown in FIG. 3, that aids in the containment of contaminants. During a colonoscopy, particles forced out of the colon can become aerosolized, meaning they become suspended in and transported through the air. Without means to prevent this aerosolization, and the inhalation by the patient and medical personnel of these contaminants, the risk of infection during a colonoscopy is greatly increased. Together with the sealing power of the continuously adhesive drape surface mentioned above, the seal between valve 30 and opening 16 at ledge 18 work together to reduce the risk of contamination.

Figure 3:
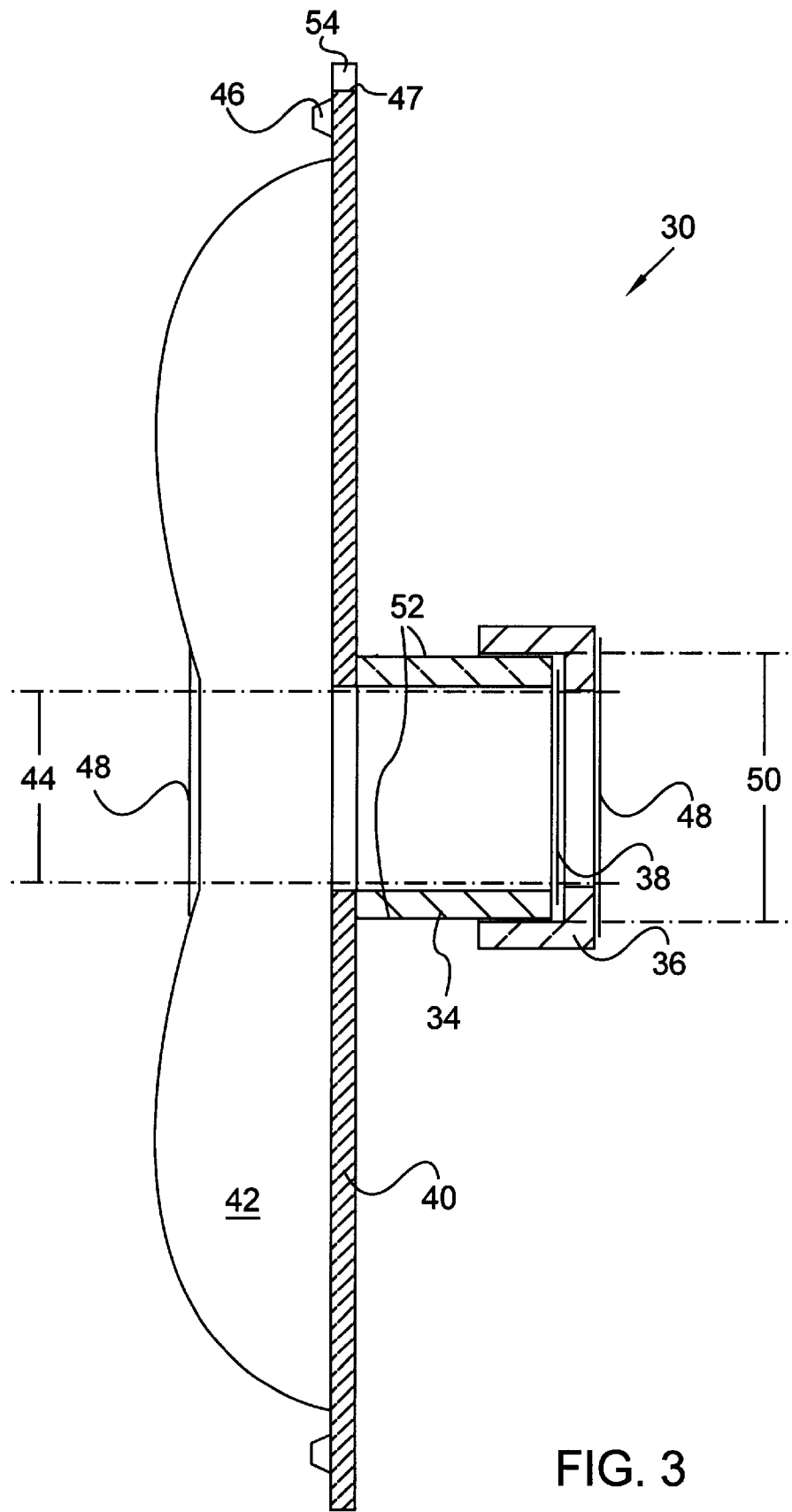
FIG. 3 is a cross-sectional view of the valve alone.

With reference to FIG. 3, valve 30 comprises tube section 34, cap 36, membrane 38, disk section 40, reservoir 42, hollow column 44, gasket 46, and peel-off stickers 48. It will be convenient to think of valve 30 as having a cap side and a reservoir side, with disk section 40 delineating the boundary between the two. Tube section 34 has a top end covered by cap 36 and a bottom end adjacent to disk section 40. Hollow column 44 is located centrally in valve 30 and extends all the way through it, thus centrally penetrating cap 36, membrane 38, tube section 34, disk section 40, and reservoir 42. Cap 36 has inner diameter 50 suitable to snugly engage outer walls 52 of tube section 34 and is securely fastened thereon. The sides of cap 36 have a length sufficient to extend parallel to and cover some portion of outer walls 52 as shown.

Membrane 38 lies interior to cap 36 and across the end of tube section 34. Membrane 38 acts as a barrier, but only a partial barrier because it is penetrated by hollow column 44 as explained above, to the flow of the substance contained in reservoir 42. Hollow column 44, where it penetrates membrane 38, narrows to a diameter sufficient to contact the colonoscope about its periphery as the colonoscope is inserted therethrough.

Disk section 40 is disposed on the bottom end of tube section 34 and acts to stabilize valve 30 and, in a preferred embodiment, houses cutouts 54, indicated in this FIG. 3 by the piece of disk section 40 above solid line 47. Cutout 54 is in the background with respect to the portion of disk section 40 shown below solid line 47. Cutouts 54 form part of one embodiment of a locking mechanism, as further illustrated in connection with FIG. 4.

Reservoir 42 depends from disk section 40 and is securely attached thereto. It is designed to be filled with a lubricating substance which, in practice, flows beyond the putative boundaries of reservoir 42 and fills all the empty space in valve 30. The hollow portions of each component of valve 30 are in effect extensions of reservoir 42 because those hollow portions are continuous with the cavity of reservoir 42.

Gasket 46 is situated on the reservoir side of disk section 40 and forms a ring around reservoir 42. When valve 30 is positioned in opening 16 of drape 10, gasket 46 settles onto ledge 18, shown in FIG. 1, and forms a substantially airtight seal between the drape components. Peel-off stickers 48 are disposed over both ends of hollow column 44 and act as a barrier preventing the solution of reservoir 42 from leaking out of valve 30.

The use of the present invention is as follows. Peel-off stickers 48 are removed and a colonoscope is threaded through valve 30 from the cap side. Although such is not the case elsewhere along its length, hollow column 44 has a diameter slightly smaller than that of the colonoscope where hollow column 44 passes through membrane 38. This means that the colonoscope stretches membrane 38 as it goes through, causing membrane 38 to tightly grip the sides of the colonoscope and largely prevent any leakage of the reservoir contents around it. The colonoscope is further passed through tube section 34 and reservoir 42 where it becomes coated with the lubricating substance stored in reservoir 44. Note that as it passes through valve 30, the colonoscope is completely surrounded with lubricating material. The colonoscope can thus be smoothly fed into or partially withdrawn from the colon as needed in order to carry out the examination, passing through valve 30 before entering the patient's body.

Cap 36, tube section 34, and disk section 40 are typically, but not necessarily, made of hard plastic. Membrane 38 is preferably made of a rubbery, pliable material such as is used to make surgical gloves. Reservoir 42 is preferentially made of a plastic sturdy enough to hold its shape but flexible enough to give somewhat when in contact with a patient's body. These characteristics minimize discomfort while providing a reliable lubricant depository.

Figure 4:
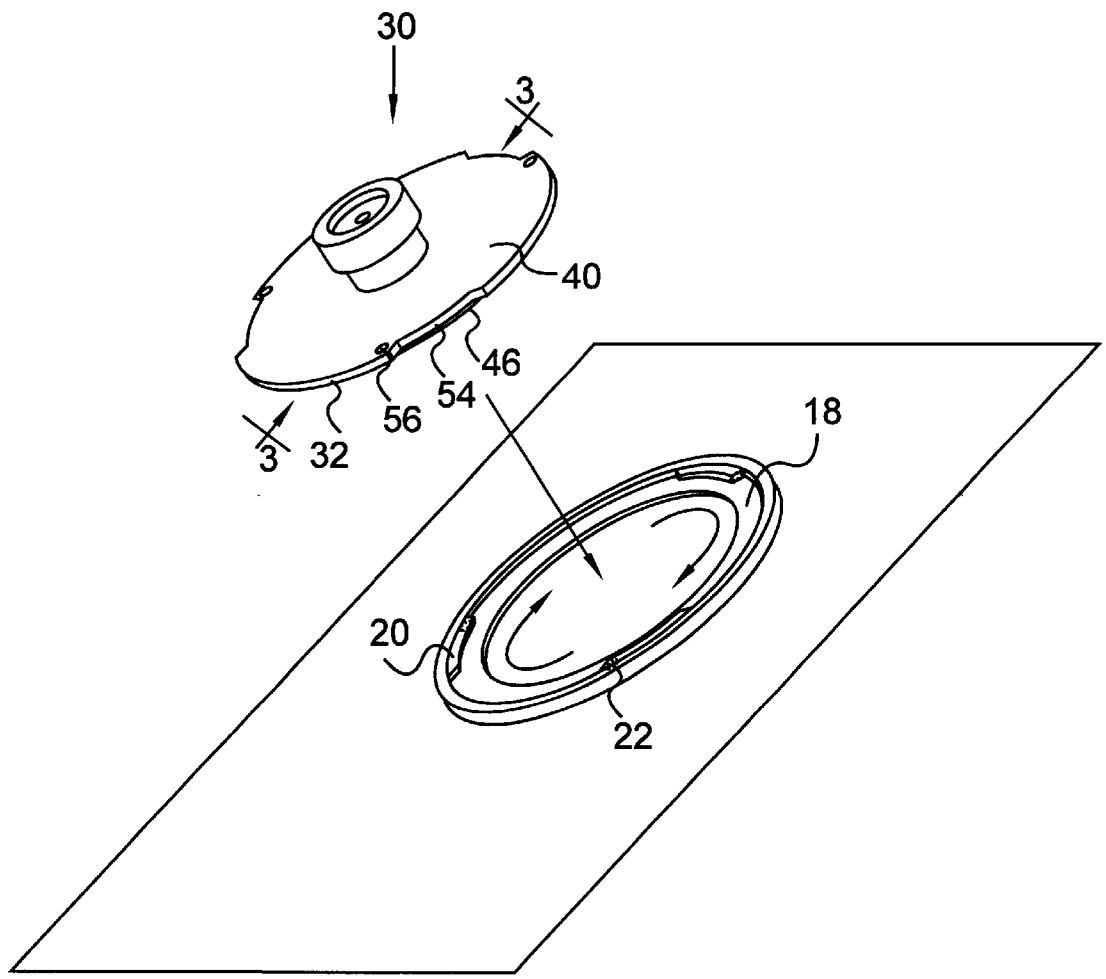
FIG. 4 is an exploded view of the valve and the opening in the drape showing one embodiment of the locking mechanism.

Referring now to FIG. 4, which shows one embodiment of the valve locking mechanism, disk section 40 of valve 30 has cutouts 54, corresponding in shape and number to flanges 20 of opening 16. Cutouts 54 receive and fit over flanges 20. Flange fingers 22, located on the underside of flanges 20 and on their leading edge in a clockwise sense, allow valve 30 to be locked into place, as will be further explained in a subsequent paragraph. Indentations 56 appear on the upper face of disk section 40 as shown and are designed to receive flange fingers 22.

It is a feature of the present invention to contain contaminants in a sealed-off area such that they remain separated from the patient and medical personnel. In order to guard against inadvertent breakage of that seal it is desirable that valve 30 lock into opening 16. The following description portrays one embodiment of the locking mechanism. It should be understood that other locking methods are also possible.

Valve 30 is moved into place by aligning cutouts 54 with flanges 20. Valve 30 is then dropped down over flanges 20 so that gasket 46 is resting on ledge 18. Valve 30 is then rotated clockwise, forcing periphery 32 underneath flanges 20. Flange fingers 22 are disposed on the leading edges, in a clockwise sense, of flanges 20 and correspond in shape and number to indentations 56 on the upper surface of disk section 40. Flange fingers 22 are located on tie underside of flanges 20, meaning they extend away from flanges 20 towards adhesive side 14 of drape 10. As valve 30 is rotated clockwise, indentations 56, located immediately in front of the leading edges of cutouts 54, approach flange fingers 22. When valve 30 is rotated far enough that indentations 56 lie directly under flange fingers 22, indentations 56 slip down over the top of flange fingers 22 and prevent valve 30 from further rotation in either direction. To be released from its locked position, valve 30 must be pressed downward far enough that indentations 56 disengage flange fingers 22. The downward pressure must be maintained until valve 30 has been rotated far enough that no portion of indentations 56 are positioned under flange fingers 22. After valve 30 has been rotated to that degree the downward pressure needed to that point may be released. Note that because valve 30 rotates freely about the colonoscope inserted therethrough, disengagement of the locking flanges and realignment of cutouts 54 with flanges 20 can be accomplished by a rotation in either direction, i.e., either clockwise or counterclockwise. This applies equally to the locking procedure, notwithstanding the fact that the arrows in FIG. 4 and the above description portray the rotation being in the clockwise direction.

Figure 5:
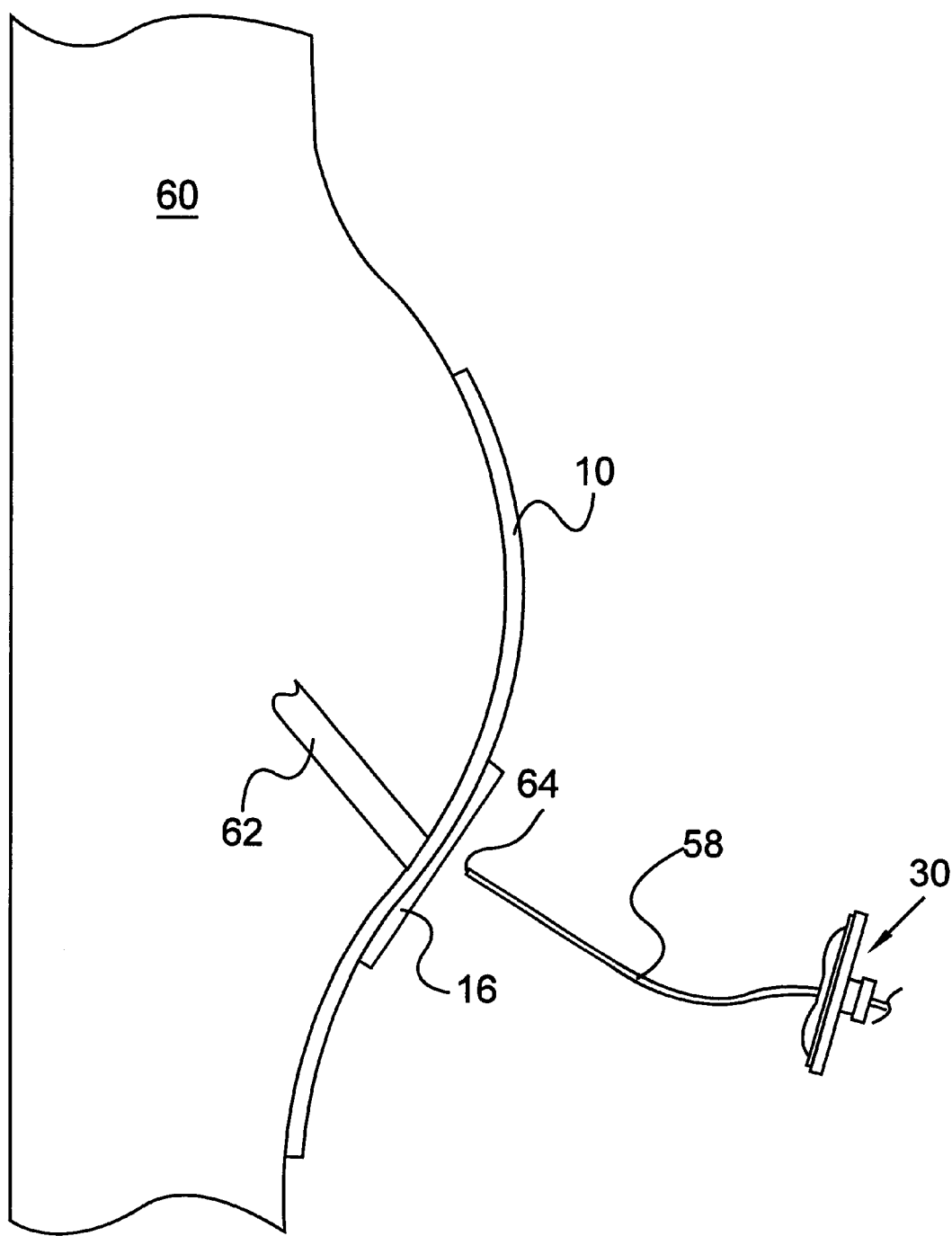
FIG. 5 is a perspective view of the drape in operation showing the colonoscope inserted through the valve and the valve temporarily positioned out of the way where it will not obstruct the physician's view.

Referring to FIG. 5, valve 30 is shown about colonoscope 58, which has tip 64. Patient 60 has colon 62. A medical worker using the present invention first removes the non-adhesive peel-off cover from adhesive side 14 of drape 10. Drape 10 is then positioned so that opening 16, with valve 30 removed, lies over the buttocks and perineal area of patient 60, with the anus centered in opening 16. Placing drape 10 in this manner allows direct visualization of the insertion point, making that process much easier than it would be if valve 30 were not removable. After pressing drape 10 into place so that it adheres to patient 60, the medical worker passes colonoscope 58 through valve 30 as explained in connection with FIG. 3. Valve 30 is pushed up colonoscope 58 a sufficient distance to be out of the way during the following step. Tip 64 of colonoscope 58 is inserted a short distance into the anus of patient 60. As noted above, opening 16 and the removability of valve 30 allow the medical worker an unobstructed view during this process.

After two or three centimeters of colonoscope 58 have been inserted as described above, the medical worker slides valve 30 back down colonoscope 58 and places it in opening 16. Valve 30 is then locked into place as described in connection with FIG. 4 and an airtight seal is formed between valve 30 and opening 16. Drape 10 then acts as a barrier, shielding patient 60, medical personnel, and anyone else in the examination room from substantially all contaminants that the colonoscopy gives rise to. The containment area is bounded on all sides by the periphery of drape 10, adhesive side 14 being attached to patient 60 such that any air leaks are insignificantly small. The seal between valve 30 and opening 16 prevents contaminants from escaping drape 10 in that region, and the snug engagement between hollow column 44 and colonoscope 58 acts to arrest any contaminant leakage through that orifice. The present invention thus offers significant protection from contamination.

While the invention has been particularly shown and described with reference to preferred embodiments thereof, it will be understood by those skilled in the art that various changes in form and details, such as those that were mentioned in the preceding pages, may be made therein without departing from the spirit and scope of the invention.

I claim:

1. A surgical drape capable of being removably secured to a patient, said drape forming a substantially fluid-impermeable barrier designed to be interposed between said patient and a medical worker thereby protecting said medical worker from a patient's excretions during a medical procedure, said drape containing an opening through which an instrument can be inserted, said drape forming a pliable, deformable sheet sized to engage a sufficient area of said patient's body as to provide said medical worker with substantial occlusive protection, said drape having an adhesive side and a non-adhesive side, said adhesive side being adhesive across substantially its entire surface, said adhesive forming a complete seal around said opening, thus reducing the possibility for contamination from aerosolized contaminants.

2. The surgical drape of claim 1 where said adhesive side is covered by an easily-removable non-adhesive layer.

3. The surgical drape of claim 2 where said easily-removable non-adhesive layer is made of absorbent material and is adapted to cover the table upon which the patient is placed.

4. The surgical drape of claim 1 where said instrument is a colonoscope.

5. The surgical drape of claim 1 where said adhesive has a strength sufficient to adhere securely to a patient's skin or clothing and to be removed from said skin or clothing without causing damage to said clothing or pain to said patient.

6. The surgical drape of claim 1 where said opening is an "O" ring.

7. The surgical drape of claim 1 where said drape is made of a see-through material.

8. The surgical drape of claim 1 where said adhesive side of said drape includes a pocket having an exterior and an interior surface, said exterior surface being adhesive and said interior surface being non-adhesive, said exterior surface further having an upper face and a lower face, said upper face being in contiguous contact with said adhesive side of said drape.

9. The surgical drape of claim 8 where said pocket is designed to catch and collect excretions or other fluid that pass from said patient.

10. A surgical drape capable of being removably secured to a patient, said drape forming a substantially fluid-impermeable barrier designed to be interposed between said patient and a medical worker thereby protecting said medical worker from a patient's excretions during a medical procedure, said drape containing a closeable opening designed to close about an instrument inserted therethrough, said opening adapted to slidably engage said instrument, wherein said opening is closed by the insertion of a removable valve that fits sealingly in said opening and through which said instrument is inserted, said drape forming a pliable, deformable sheet sized to engage a sufficient area of said patient's body as to provide said medical worker with substantial occlusive protection.

11. The invention of claim 10 wherein said opening is closed by the insertion of a valve that fits sealingly in said opening and through which the instrument is inserted.

12. The invention surgical drape of claim 10 wherein said removable valve has a hollow column to receive said instrument, said valve capable of being repeatedly and easily removed from and returned to said opening.

13. The surgical drape of claim 12 where said hollow column is sized to slidably engage said instrument such that there is sufficient sealing around said instrument to substantially eliminate the passage of excretions through said drape.

14. The surgical drape of claim 12 where said removable valve comprises:

a tube section having a top end and a bottom end;

a cap covering said top end of said tube section, said cap having inside diameter sufficient to snugly engage a portion of said tube section and length sufficient to extend from said top end some distance down the vertical walls of said tube section towards said bottom end;

a membrane disposed interior to said cap, said membrane forming a flexible barrier across said top end of said tube section, said membrane being held in place by said cap;

a disk section disposed on said bottom end of said tube section;

a reservoir depending from said disk section, said reservoir defining a cavity, said cavity provided with a lubricating solution prior to the use of said surgical drape in a medical procedure;

a gasket attached to said disk section forming a ring around said reservoir;

a hollow column disposed in a central region of said valve, said hollow column extending from said cap, through said membrane, tube section, disk section, and reservoir, said hollow column suitable for receiving and slidably engaging an instrument; said hollow column having a top end forming a hole in said cap and a bottom end forming a hole in said reservoir; and first and second peel-off stickers, said first peel-off sticker disposed so as to cover said top end of said hollow column, said second peel-off sticker disposed so as to cover said bottom end of said hollow column.

15. The surgical drape of claim 12 where said adhesive side of said drape is adhesive across substantially its entire surface.

16. The surgical drape of claim 13 further comprising a reservoir, said reservoir provided with a lubricating solution prior to the use of said surgical drape in a medical procedure.

17. The surgical drape of claim 14 further comprising a locking mechanism whereby said valve is designed to be locked into place.

18. The valve of claim 14 where said disk section is made of transparent material.

19. The locking mechanism of claim 17 where said locking mechanism can be released only through the application of some pressure tending to cause said opening to be moved in a direction opposite to said valve.

20. The surgical drape of claim 10 where said instrument is a colonoscope.

21. The surgical drape of claim 10 where said drape has an adhesive side and a non-adhesive side, said adhesive side being adhesive across substantially its entire surface.

* * * * *